United States Patent [19]

Ogawa et al.

[11] Patent Number: 5,011,963
[45] Date of Patent: Apr. 30, 1991

[54] TERMINAL PERFLUOROALKYLSILANE COMPOUNDS

[75] Inventors: Kazufumi Ogawa; Hideharu Tamura, both of Kadoma; Toshinobu Ishihara, Chiyoda; Yasuhisa Tanaka, Chiyoda; Mikio Endou, Chiyoda, all of Japan

[73] Assignees: Matsushita Electric Ind., Co., Ltd., Osaka; Shin-etsu Chemical Co., Ltd., Tokyo, both of Japan

[21] Appl. No.: 307,968

[22] Filed: Feb. 9, 1989

[30] Foreign Application Priority Data

Feb. 9, 1988 [JP] Japan ................... 63-27952

[51] Int. Cl.$^5$ ............................ C07F 7/08; C07F 7/18
[52] U.S. Cl. ........................ 556/485; 556/488
[58] Field of Search ........................ 556/485, 488

[56] References Cited

U.S. PATENT DOCUMENTS

| | | | |
|---|---|---|---|
| 3,012,006 | 12/1961 | Holbrook et al. | 556/485 X |
| 3,015,585 | 1/1962 | Holbrook et al. | 556/485 X |
| 3,188,336 | 6/1965 | Haszeldine | 556/485 X |
| 3,298,997 | 1/1967 | Holbrook | 556/485 X |
| 4,384,100 | 5/1983 | Takamizawa et al. | 556/485 X |

FOREIGN PATENT DOCUMENTS 2511187  9/1975  Fed. Rep. of Germany ...... 556/485

*Primary Examiner*—Paul F. Shaver
*Attorney, Agent, or Firm*—Parkhurst, Wendel, Rossi

[57] ABSTRACT

A terminal perfluoroalkylsilane compound $F(CF_2)_m(CH_2)_nSi(CH_3)_pX_{3-p}$ (m+n=10 to 32 carbon atoms in fluoroalkyl group) is prepared by a hydrosilylation reaction of a terminal perfluoroalkene compounds $F(CF_2)_m(CH_2)_{1+q}CH=CH_2$ (1+q+2=n) with the hydrodiensilane $HSi(CH_3)_pX^3_{3-p}$. The $F(CF_2)_m(CH_2)_{1+q}CH=CH_2$ are synthesized by a Grignard's reaction of a Grignard's reagent $X^2Mg(CH_2)_qCH=CH_2$ obtained from a terminal alkenyl halogen compound $X^2(CH_2)_qCH=CH_2$ with a terminal fluoroalkyl halogen compound $F(CF_2)_m(CH_2)_1X^1$.

The terminal perfluoroalkylsilane compound has a sufficient lubricating effect and is useful for a coating agent with long and continuous lubricity.

4 Claims, 1 Drawing Sheet

TERMINAL PERFLUOROALKYLSILANE COMPOUNDS

BACKGROUND OF THE INVENTION

This invention relates to terminal perfluoroalkylsilane compounds, methods of preparing these compounds, and coating agents using such compounds.

Conventional terminal perfluoroalkylsilane compounds were manufactured as follows. For instance, such perfluoroalkene compound as $C_4F_9CH=CH_2$ or $C_8F_{17}CH=CH_2$ is allowed to react, with platinum as catalyst and through hydrosilylation, with $HSi(CH_3)Cl_2$ or $HSiCl_3$ to synthesize into terminal perfluoroalkylsilane $C_4F_9(CH_2)_2Si(CH_3)Cl_2$ or $C_8F_{17}(CH_2)_2 SiCl_3$. The terminal perfluoroalkylsilane compounds obtained by the above process are however limited to compounds of ten or less carbon atoms in the fluoroalkyl group bonded to silicon atom. The perfluoroalkene compounds may be produced as intermediate products or byproducts in the process of fluorocarbon resin industry.

Magnetic recording materials of mediums as magnetic disks or tapes have magnetic film applied with coating agent on the surface of which a lubricating layer is formed. This is however problematical because the capability of the lubricating layer may be reduced due to its deviation, splashing and/or evaporation thereof by displacement of coating agent. Though diverse coating agents to be applied under low vapor pressure have been used for that reason, this could not lead to a drastic resilution of the problem.

As the compounds having fluoroalkyl groups have been observed to be excellent in lubricity, the inventors of the present invention performed a study for forming a lubricating layer on a magnetic film applying terminal perfluoroalkylsilane compounds as coating agents, thereon. Use of conventional terminal perfluoroalkylsilane compounds cannot give a satisfying lubricating effect though. Further such defects were discovered as unevenness and pinholes on the lubricating layer and/or poor durability thereof. As a result of thorough investigations and studies of the reasons of the defects, it has eventually been revealed the following. Terminal perfluoroalkylsilane compound, sillane coupled with an inorganic substance on the magnetic film, forms a monomolecular film. However, the conventional terminal perfluoroalkylsilane compounds cannot form a uniform film when used as a coating agent since the compounds have only ten or less carbon atoms in their fluoroalkyl group bonded to the silicon atom, as mentioned above. It is conceivable that the abovementioned defects of insufficient lubricating effect may be caused.

Inventors of the present invention anticipated that if a fluoroalkyl group bonded to the silicon atom being long enough in a terminal perfluoroalkylsilane compound, it would be excellent as a coating agent. But there never existed terminal perfluoroalkylsilane compounds meeting such a condition. Moreover, perfluoroalkene compounds, which were intermediate products for synthesizing terminal perfluoroalkylsilane compounds, never had long enough chain molecules. In addition, the number of fluorine in the perfluoroalkene compounds have been limited.

The inventors took up a presupposition as below.

First, a terminal perfluoroalkyl compound $F(CF_2)_m(CH_2)_nX^1$ ($X^1$ is I, Br or Cl) with longer chain molecules could be synthesized from starting material of available terminal perfluoroalkyl compound having relatively short chain such as $F(CF_2)_2CH_2I$, $F(CF_2)_2CH_2Cl$, or $F(CF_2)_3I$. Then Grignard's reagent $F(CF_2)_m(CH_2)_nMgX^1$ would be synthesized therefrom. This reagent, when allowed to react with $(CH_3)_pSiX^3{}_{4-p}$ (p is an integral number between 2 and 4, $X^3$ is I, Br, Cl or alkoxyl group), would lead to a synthesis of a terminal perfluoroalkylsilane compound having longer chain. Although the inventors tried the experimentation of this process of the presupposition. Grignard's reagent could not be stably synthesized from the $F(CF_2)_2CH_2X^1$, $F(CF_2)_3X^1$ nor from $F(CF_2)_m(CH_2)_nX^1$. Therefore, a terminal perfluoroalkylsilane compound having long chain molecules of fluoroalkyl group could not be synthesized.

SUMMARY OF THE INVENTION

An object of the present invention is to provide a terminal perfluoroalkylsilane compounds having a long enough fluoroalkyl group bonded to a silicone atom, which are represented by a general formula:

$$F(CF_2)_m(CH_2)_nSi(CH_3)_pX_{3-p} \tag{1}$$

$m=1$ to 8, $m+n=10$ to 32, $p=0$ to 2 of each integral number, X is a halogen atom select from I, Br and Cl, or an alkoxy group, which should preferably be methoxy group or ethoxy group.

An example of the aforesaid terminal perfluoroalkylsilane compound is ω-trifluoroalkylsilane compound, which is represented by the following general formula:

$$CF_3(CH_2)_nSi(CH_3)_pX_{3-p} \tag{2}$$

that is standing for $m=1$ in the formula (1) above. In this formula (2), $n=9$ to 31, $p=0$ to 2 of each integral number, and X is a halogen atom selected from I, Br and Cl, or an alkoxyl group.

Another object of the invention is to provide a suitable method for preparing a terminal perfluoroalkylsilane compound.

The method includes a process through which a terminal perfluoroalkene compound represented by the following general formula:

$$F(CF_2)_m(CH_2)_{1+q}CH=CH_2 \tag{3a}$$

is obtained by allowing a terminal perfluoroalkyl halogen compound represented by the following general formula:

$$F(CF_2)_m(CH_2)_lX^1 \tag{3b}$$

(where $m=1$ to 8, $l=0$ to 2 of each integral number, $X^1$ stands for a halogen atom selected from I, Br and Cl) to react with a Grignard's reagent:

$$X^2Mg(CH_2)_qCH=CH_2 \tag{3c}$$

which is synthesized from a terminal alkenyl halogen compound represented by;

$$X^2(CH_2)_qCH=CH_2 \tag{3d}$$

($q=8$ to $30-(m+1)$ of an integral number, $X^2$ stands for a halogen atom selected from I, Br and Cl), and which also includes another process wherein such terminal perfluoroalkene compound as indicated by the general formula (3a) above reacts, through hydrosilylation, with hydrodienesilane to be represented by the following formula:

$$HSi(CH_3)_p X^3{}_{3-p} \qquad (3e)$$

(p=0 to 2 of an integral number), $X^3$ stand for a halogen atom selected from I, Br and Cl, or an alkoxyl group).

The method for preparing the ω-trifluoroalkylsilane compound as expressed by the above formula (2) has a process through which ω-trifluoroalkene compound represented by the following formula:

$$CF_3(CH_2)_r CH=CH_2 \qquad (4)$$

(r=7 to 29 of an integral number) reacts, through hydrosilylation, with hydrodienesilane expressed by the formula (3e).

Further object of the invention is to provide a coating agent containing a terminal perfluoroalkysilane compound having 10 to 32 carbon atoms its fluoroalkyl group which is characterized by its sufficient lubricating effect and durability.

DETAILED DESCRIPTION OF THE INVENTION

Figure 1:
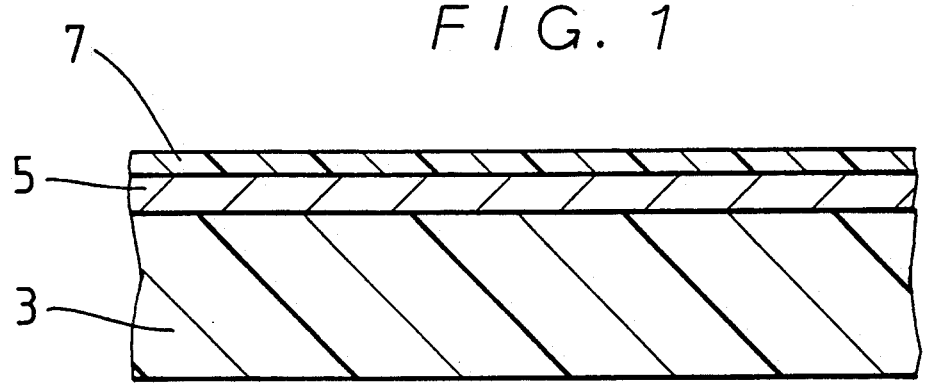
FIG. 1 is an enlarged sectional view of an example where a coating agent by this invention is used.

The short-chained terminal perfluoroalkylhalogen compounds expressed by the formula (3b) above, which are starting materials to produce such terminal perfluoroalkyl halogen compounds as under the formula (1), are available in the market. Some examples of the formula (3b) may be enumerated: $F(CF_2)_2CH_2Cl$ (2,2,3,3,3-pentafluoropropyl chloride), $F(CF_2)_2CH_2I$ (2,2,3,3,3-pentafluoropropyl iodide), $F(CF_2)_3I$ (perfluoropropyl iodide), $F(CF_2)_3CH_2Br$ (2,2,3,3,4,4,4-heptafluorobutyl bromide).

The terminal alkenyl halogen compounds expressed by the above formula (3d) are, for instance, $Cl(CH_2)_{10}CH=CH_2$ (11-dodecenyl chloride), $Cl(CH_2)_{14}CH=CH_2$ (15-hexadecenylchloride), $Br(CH_2)_{17}CH=CH_2$ (18-nonadecenyl bromide). In the similar way, the hydrodienesilane represented by the formula (3e) is, for instance, $HSiCl_3$ (trichlorosilane), $HSi(CH_3)Cl_2$ (methyldichlorosilane), $HSi(CH_3)_2Cl$ (dimethylchlorosilane), $HSi(OCH_3)_3$ (trimethoxysilane) and $HSiCH_3(OC_2H_5)_2$ (methyldiethoxysilane).

As the terminal perfluoroalkylsilane represented by the formula (1), which can be prepared from the respective substances as above, there exist, for example, $F(CF_2)_2(CH_2)_{13}Si(CH_3)Cl_2$ (14,14,15,15,15-pentafluoropentadecylmethyldichlorosilane), $F(CF_2)_2(CH_2)_{17}SiCl_3$ (18,18,19,19,19-pentafluorononadecyltrichlorosilane), $F(CF_2)_3(CH_2)_{16}Si(OCH_3)_3$ (17,17,18,18,19,19,19-heptafluorononadecyltrimethoxysilane).

The Grignard's reagent as under the above formula (3c) is elaborated as follows. Metallic magnesium is put into diethylether or tetrahydrofuran prepared beforehand as a reactive solvent. The reagent can be synthesized, as the terminal alkenyl halogen compound as under the formula (3d) is supplied thereinto. The volume of the metallic magnesium should preferably be of same mol or slightly higher mol than the terminal alkenyl haloagen compound.

The terminal perfluoroalkene compound as the formula (3a) is synthesized by the Grignard's reagent as under (3c) formula reacting with the terminal perfluoroalkyl halogen compound expressed by (3b) formula. As the same with the foregoing example, the terminal perfluoroalkyl halogen compound (3b) is put beforehand into such reactive solvent as diethylether or tetrahydrofuran and thereinto the aforesaid Grignard's reagent is to be added slowly. Reversely the Grignard's reagent is put beforehand into a reactive solvent, into which the terminal perfluoroalkyl halogen compound may be added afterwards. Copper may also be put into as a catalyst. Upon termination of the reaction, aqua is added to the reaction system, and the organic layer shall be separated from aqueous layer after dissolving the magnesium salt there produced into the aqueous solution. The terminal perfluoroalkene compound under the formula (3a) can be obtained by stripping out from said organic layer such low boiling substance as reactive solvent. Purification by distillation may be applicable wherever practicable.

The hydrosilylation reaction between the terminal perfluoroalkene compound under (3a) and the hydrodienesilane (3a) give the terminal perfluoroalkylsilane as (1), which is an objective. Since having been described above, the synthesis of the terminal perfluoroalkene compound requires a long time, we will lose much if we leave any substance unreacted. Not to leave such substance at all and for other purpose, the hydrodienesilane should be added in excessive volume for due reaction. Preferably this reaction should be made under existence of platinum catalyst. In the event that the reaction system is under normal pressure, reaction is made under reflux. The reaction may be made in an autoclave if it is to be performed under pressurization or depressurization. From viewpoints of economy and safety, preferably, the hydrodienesilane is continuously supplied into the terminal perfluoroalkene compound under the existence of a catalyst for desired reaction in industrial process. If necessary, hydrocarbon solvent such as inactive n-hexane and toluene may be used in the reaction system. The terminal perfluoroalkylsilane compound of the formula (1) can be prepared in good purity by stripping out such low boiling matter as unreacted substance and reactive solvent. Purification by distillation may be performed wherever applicable.

In order that the terminal perfluoroalkylsilane as obtained by the foregoing process may be effectively used as coating agent, the following method should preferably be applied. First of all the terminal perfluoroalkylsilane is dissolved into such organic solvent as n-hexane, toluene, chloroform and carbon tetrachloride. Into this solution, magnetic disks or magnetic tapes to be coated will be dipped. It is also possible to spray or brush this solution onto an article to be coated. Application by roller is practicable too. Coating then is accomplished after the article is dried up under normal temperature or heat.

Coating of the terminal perfluoroalkylsilane compound may be used not only on the magnetic recording materials but in coating intended for lubricity and mold release characteristics, in particular for protective coat for optical fiber and condenser.

FIG. 1 is an enlarged sectional view of a magnetic disk with its coating accomplished. As is seen in this figure a magnetic filim 5 on a base plate 3 is covered by the lubricating layer 7 of the terminal perfluoroalkylsilane. This magnetic film 5 may be covered by another protective film on which the lubricating layer 7 of terminal perfluoroalkylsilane compound may be formed.

Figure 2:
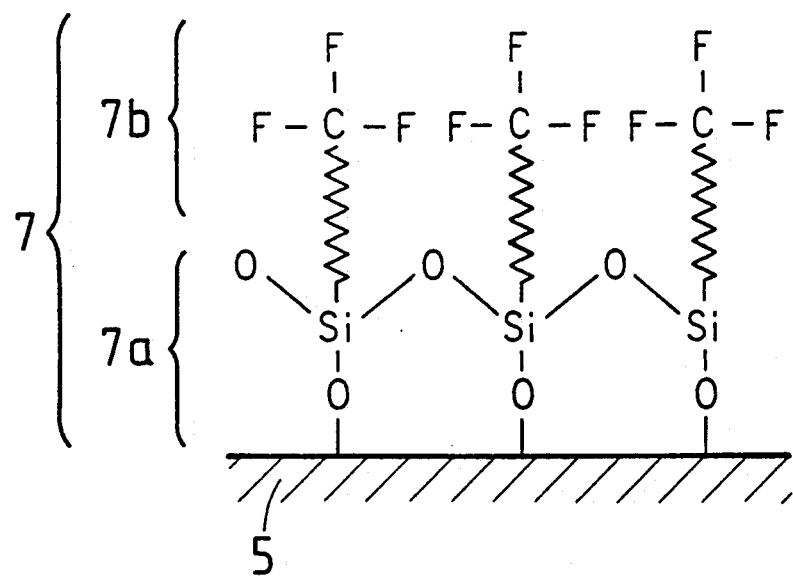
FIG. 2 is an enlarged scheme of the same example.

FIG. 2 represents an enlarged scheme of the magnetic film 5 and the terminal perfluoroalkylsilane compound of the lubricating layer 7. As shown in this figure, the lubricating layer 7 covering the surface of the magnetic film 5 consists of monomolecular film of the terminal perfluoroalkylsilane. The Si—X bond of the terminal perfluoroalkylsilane compound shown by the formula (1) is hydrolytic, and thus silane-couples with inorganic substance on the magnetic film 5 while its hydrolyzing. Therefore fluoroalkyl group comes toward the surface for the compound to form monomolecular film. The layer 7a in FIG. 2 corresponds to the silane-coupling and the layer 7b is corresponds to the fluoroalkyl group.

Since the fluoroalkyl group excellent in lubricity is directed toward the surface, the lubricating layer 7 becomes excellent in lubricity. Since furthermore the carbon atom number of the fluoroalkyl group in the terminal perfluoroalkylsilane compound is suitable (10 to 32), a uniform lubricating layer 7 without any pinhole can form. Note the fact that if the carbon atom number is 10 or less, this will result in insufficient thickness of the monomolecular film, namely the lubricating layer 7. If, on the other hand, the same number is 32 or more, then the lubricating layer 7 will become uneven losing surface smoothness because too long molecular chains entangle themselves each other. Moreover since the magnetic film 5 and the lubricating layer 7 are silane-coupled, this consolidated bond prevents splashing, evaporation or similar adverse phenomenon, thereby remarkably contributing to the longer durability.

Some preferable working examples are shown hereunder.

WORKING EXAMPLE 1

Metallic magnesium 12.0 g (0.5 mol) and tetrahydrofuran 200 ml were put into a reaction vessel consisting of a 500 ml flask, stirrer, thermometer, reflux condenser and dropping funnel. 129.3 g (0.5 mol) of $Cl(CH_2)_{14}CH=CH_2$ (15-hexadecenyl chloride) was dropped thereinto at 50° C. to 60° C. for two hours. One hour of maturing of this at 60° to 70° C. then could synthesize $ClMg(CH_2)_{14}CH=CH_2$ of Grignard's reagent.

200 ml of tetrahydrofuran was put into a similar reaction vessel having 1 lit. of flask, into which 0.5 g of LiCl and 0.7 g of $CuCl_2$ were dissolved, and 106.5 g (0.5 mol) of $F(CF_2)_2CH_2Br$ (2,2,3,3,3-pentafluoropropyl bromide) was then added. After ice cooling these, said Grignard's reagent was dropped thereinto at 20° C. or less for one hour and then matured at 30° C. for one hour. Measurement of this reaction solution by gas chromatography revealed 95% of reaction rate. An aqueous solution of 5% hydrochloric acid was added into this reaction solution and they were mixed to dissolve the magnesium salt produced in the reaction solution. The solution mixture thereof is left standing to separate into an aqueous layer and an organic layer, and this latter is taken out. After stripping out the solvent tetrahydrofuran from the organic layer, vacuum distillation soled to production of 95% purity of $F(CF_2)_2(CH_2)_{15}CH=CH_2$ (18,18,19,19,19-pentafluorononadecene) with 85% of yield.

35.6 g (0.1 mol) of the $F(CF_2)_2(CH_2)_{15}CH=CH_2$ thus obtained and 0.04 g of 20% $H_2PtCl_6 \cdot 6H_2O$ in isopropyl alcohol solution were prepared into a similar reaction vessel having 100 ml of flask. 27.1 g (0.2 mol) of $HSiCl_3$ (trichlorosilane) was dropped thereinto at 100° to 110° C. for five hours. Then three hours of maturation was made at 120° C. Simple vacuum distillation of this reaction liquid produced 96% purity of $F(CF_2)_2(CH_2)_{17}SiCl_3$ (18,18,19,19,19-pentafluorononadecyl trichlorosilane) with 83% of yield.

WORKING EXAMPLE 2

By the same way as Working Example 1, the Grignard's reagent $ClMg(CH_2)_{14}CH=CH_2$ was synthesized, except that the volume of tetrahydrofuran was increased to 400 ml into a reaction vessel same as Working Example 1 having one lit. of flask.

Then this reagent was ice cooled, into which 148.0 g (0.5 mol) of $F(CF_2)_3I$ (perfluoropropyl iodide) was dropped at 20° C. or less for one hour, and then maturation was performed at 30° C. for one hour. Measurement of this reaction solution by gas chromatography revealed 98% of reaction rate. Then, as in the case of Working Example 1, the magnesium salt was dissolved and separated. After stripping out low boiling substance from an organic layer, vacuum distillation produced 97% purity of $F(CF_2)_3(CH_2)_{14}CH=CH_2$ (17,17,18,18,19,19,19-heptafluorononadecene) with 88% of yield.

39.2 g (0.1 mol) of the $F(CF_2)_3(CH_2)_{14}CH=CH_2$ and 0.05 g of 20% $H_2PtCl_6 \cdot 6H_2O$ in isopropyl alcohol solution were put into a reaction vessel of 100 ml, same with Working Example 1. Then 18.3 g (0.15 mol) of $HSi(OCH_3)_3$ (trimethoxysilane) was dropped thereinto at 100° to 110° C. for six hours. Five hours of maturation was performed thereafter at 120° C. Vacuum distillation of this reaction liquid could produced 95% purity of $F(CF_2)_3(CH_2)_{16}Si(OCH_3)_3$ (17,17,18,18,19,19,19-heptafluorononadecyl trimethoxysilane) with 83% of yield.

WORKING EXAMPLE 3

The Grignard's reagent $ClMg(CH_2)_{10}CH=CH_2$ was synthesized by using 101.3 g (0.5 mol) of $Cl(CH_2)_{10}CH=CH_2$ (11-dodecenyl chloride) substituting by $Cl(CH_2)_{14}CH=CH_2$ of the Working Example 1 in a vessel of the same as Working Example 1 having 400 ml of flask.

200 ml of tetrahydrofuran was put into a similar reaction vessel having 1 lit. of flask, into which 0.5 g of LiCl and 0.7 g of $CuCl_2$ were dissolved, and 106.5 g (0.5 mol) of $F(CF_2)_2CH_2Br$ was then added. After ice cooling these, said Grignard's reagent was dropped thereinto at 20° C. or less for one hour and then matured at 30° C. for one hour. Measurement of this reaction solution by gas chromatography revealed 96% of reaction rate. Then, as in the case of Working Example 1, the magnesium salt was dissolved and separated. After stripping out low boiling substance from an organic layer, vacuum distillation produced 95% purity of $F(CF_2)_2(CH_2)_{11}CH=CH_2$ (14,14,15,15,15-pentafluoropentadecene) with 83% of yield.

30.0 g (0.1 mol) of the $F(CF_2)_2(CH_2)_{11}CH=CH_2$ and 0.05 g of 20% $H_2PtCl_6 \cdot 6H_2O$ in isopropyl alcohol solution were put into a reaction vessel of 100 ml, same with Working Example 1. Then 23.0 g (0.2 mol) of $HSi(CH_3)Cl_2$ (methyldichlorosilane) was dropped thereinto at 100° to 110° C. for five hours. Four hours of maturation was performed thereafter at 120° C. Vacuum distillation of this reaction liquid could produced 97% purity of $F(CF_2)_2(CH_2)_{13}Si(CH_3)Cl_2$ (14,14,15,15,15-pentafluoropentadecyl methyldichlorosilane) with 83% of yield.

WORKING EXAMPLE 4

By the same way as Working Example 1, the Grignard's reagent $ClMg(CH_2)_7CH=CH_2$ was synthesized from 80.3 g (0.5 mol) of $Cl(CH_2)_7CH=CH_2$ (8-nonenyl chloride) as a material by using the volume of tetrahydrofuran increased to 400 ml into a reaction vessel same as Working Example 1 having one lit. of flask.

Then this reagent was ice cooled, into which 173.0 g (0.5 mol) of $F(CF_2)_4I$ (perfluorobutyl iodide) was dropped at 20° C. or less for one hour, and then maturation was performed at 30° C. for one hour. Measurement of this reaction solution by gas chromatography revealed 98% of reaction rate. Then, as in the case of Working Example 1, the magnesium salt was dissolved and separated. After stripping out low boiling substance from an organic layer, vacuum distillation produced 98% purity of $F(CF_2)_4(CH_2)_7CH=CH_2$ (10,10,11,11,12,12,13,13,13-nonafluorotridecene) with 90% of yield.

34.4 g (0.1 mol) of the $F(CF_2)_4(CH_2)_7CH=CH_2$ and 0.05 g of 20% $H_2PtCl_6 \cdot 6H_2O$ in isopropyl alcohol solution were put into a reaction vessel of 100 ml, same with Working Example 1. Then 20.3 g (0.15 mol) of $HSiCl_3$ was dropped thereinto at 100° to 110° C. for six hours. Three hours of maturation was performed thereafter at 120° C. Vacuum distillation of this reaction liquid could produced 97% purity of $F(CF_2)_4(CH_2)_9SiCl_3$ (10,10,11,11,12,12,13,13,13-nonafluorotridecyl trichlorosilane) with 87% of yield.

WORKING EXAMPLE 5

By the same way as Working Example 4, the Grignard's reagent $ClMg(CH_2)_{13}CH=CH_2$ was synthesized from 122.3 g (0.5 mol) of $Cl(CH_2)_{13}CH=CH_2$ (14-pentadecenyl chloride) as a material.

Under the same condition as Working Example 4, 173.0 g (0.5 mol) of $F(CF_2)_4I$ (perfluorobutyl iodide) was dropped into this synthesized Grignard's reagent, and then maturation was performed. Measurement of this reaction solution by gas chromatography revealed 98% of reaction rate. Then, as in the case of Working Example 1, the magnesium salt was dissolved and separated. After stripping out low boiling substance from an organic layer, vacuum distillation produced 97% purity of $F(CF_2)_4(CH_2)_{13}CH=CH_2$ (16,16,17,17,18,18,19,19,19-nonafluorononadecene) with 88% of yield.

42.8 g (0.1 mol) of the $F(CF_2)_4(CH_2)_{13}CH=CH_2$ and 0.05 g of 20% $H_2PtCl_6 \cdot 6H_2O$ in isopropyl alcohol solution were put into a reaction vessel of 100 ml, same with Working Example 1. Then 27.1 g (0.2 mol) of $HSiCl_3$ was dropped thereinto at 100° to 110° C. for six hours. Four hours of maturation was performed thereafter at 120° C. Vacuum distillation of this reaction liquid could produced 96% purity of $F(CF_2)_4(CH_2)_{15}SiCl_3$ (16,16,17,17,18,18,19,19,19-nonafluorononadecyl trichlorosilane) with 85% of yield.

WORKING EXAMPLE 6

By the same way as Working Example 4, 0.5 mol of the Grignard's reagent $ClMg(CH_2)_7CH=CH_2$ was synthesized.

As in the case of Working Example 1, this reagent was ice cooled, into which 273.0 g (0.5 mol) of $F(CF_2)_8I$ (perfluorooctyl iodide) was dropped at 20° C. or less for one hour, and then maturation was performed at 30° C. for one hour. Measurement of this reaction solution by gas chromatography revealed 97% of reaction rate. Then the magnesium salt was dissolved and separated. After stripping out low boiling substance from an organic layer, vacuum distillation produced 98% purity of $F(CF_2)_8(CH_2)_7CH=CH_2$ (10,10,11,11,12,12,13,13,14,14,15,15,16,16,17,17,17-heptadecafluoroheptadecene) with 90% of yield.

42.8 g (0.1 mol) of the $F(CF_2)_8(CH_2)_7CH=CH_2$ and 0.05 g of 20% $H_2PtCl_6 \cdot 6H_2O$ in isopropyl alcohol solution were put into a reaction vessel of 100 ml, same with Working Example 1. Then 27.1 g (0.2 mol) of $HSiCl_3$ was dropped thereinto at 100° to 110° C. for six hours. Four hours of maturation was performed thereafter at 120° C. Vacuum distillation of this reaction liquid could produced 97% purity of $F(CF_2)_8(CH_2)_9SiCl_3$ (10,10,11,11,12,12,13,13,14,14,15,15,16,16,17,17,17-heptadecafluoroheptadecyl trichlorosilane) with 85% of yield.

WORKING EXAMPLE 7

0.5 mol of $CF_3(CH_2)_{16}CH=CH_2$ (19,19,19-trifluorononadecene) and 0.05 g of 20% $H_2PtCl_6 \cdot 6H_2O$ in isopropyl alcohol solution were put into a reaction vessel having 300 ml of a flask same as Working Example 1. Temperature was raised up to 100° C., and 0.75 mol of $HSiCl_3$ was dropped thereinto for five hours within the temperature range of 100° to 110° C. Two hours of maturing was performed thereafter at 120° C. After cooling this reaction solution, measurement by gas chromatography using silicone type capillary column revealed that the peak of $CF_3(CH_2)_{16}CH=CH_2$ had disappeared. Distillation of the reaction solution thereafter produced, at a boiling point of 220° C./mmHg, $CF_3(CH_2)_{18}SiCl_3$ (19,19,19-trifluorononadecyl trichlorosilane). The yield thereof was 82%. The structure of the $CF_3(CH_2)_{18}SiCl_3$ thus obtained was confirmed by way of mass spectrum (MS), nuclearmagnetic resonance spectrometry (NMR) and infrared absorption spectrum (IR).

Each measured datum is as flowings:

Mass spectrum (Spectrum Ratio m/Z);
*371 (3); *231 (4); *217 (6); *203 (7); *189 (10); *175 (14); *133 (16); 97 (22); 91 (23); 85 (43); 83 (33); 71 (63); 69 (47); 57 (100); 55 (72); 43 (73); 41 (57).
*Peaks of these marks are accompanied with isotope peak of of $^{37}Cl$.

Magnetic resonance spectrometry: δ(ppm)

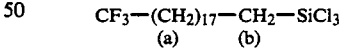

a: 1.20~2.0 ppm (M); b: 3.12 ppm (T)
Infrared absorption spectrum: $cm^{-1}$; 2920; 2850; 1470; 690.

WORKING EXAMPLE 8

0.5 mol of $CF_3(CH_2)_8CH=CH_2$ (11,11,11-trifluoroundecene) and 0.05 g of 20% $H_2PtCl_6 \cdot 6H_2O$ in isopropyl alcohol solution were put into a reaction vessel same as Working Example 7. Temperature was raised up to 100° C., and 0.75 mol of $HSiCl_3$ was dropped thereinto for five hours within the temperature range of 100° to 110° C. Two hours of maturing was performed thereafter at 120° C. After cooling this reaction solution, measurement by gas chromatography under the same condition as Working Example 7 revealed that the peak of $CF_3(CH_2)_8CH=CH_2$ had disappeared. Distillation of the reaction solution thereafter produced, at a boiling point of 220° C./mmHg, $CF_3(CH_2)_{10}SiCl_3$ (11,11,11-trifluoroundecyl trichlorosilane). The yield thereof was 82%. The structure of the $CF_3(CH_2)_{10}SiCl_3$ thus obtained was confirmed by way of mass spectrum (MS), nuclearmagnetic resonance spectrometry (NMR) and infrared absorption spectrum (IR).

Each measured datum is as flowings:

Mass spectrum (Spectrum Ratio m/Z);

*259 (8); *217 (4); *203 (12); *189 (12); *175 (30); *133 (34); 91 (38); 85 (28); 71 (40); 69 (26); 57 (64); 55 (62); 43 (100); 41 (66); 39 (20).

*Peaks of these marks are accompanied with isotope peak of of $^{37}Cl$.

Magnetic resonance spectrometry: δ(ppm)

$$CF_3-(CH_2)_9-CH_2-SiCl_3$$
$$\quad\quad\quad\quad (a)\quad\quad (b)$$

a: 1.20~1.63 ppm (M) b: 3.10 ppm (T)

Infrared absorption spectrum: $cm^{-1}$; 2930; 2860; 1470; 1215; 1180; 770; 720; 690.

The terminal perfluoroalkylsilane compounds of the above described had a sufficient lubricating effect and should be useful for a coating agent with long and continuous lubricity.

While there has been described what is at present considered to be the preferred examples of the invention, it will be understood that various modifications may be made therein, and it is intended to cover in the appended claims all such modifications as fall within the true spirit and scope of the invention.

What is claimed is:

1. A terminal perfluoroalkylsilane compound having the general formula;

$$F(CF_2)_m(CH_2)_nSi(CH_3)_pX_{3-p}$$

wherein m, n, and p are each integers; m=1 to 8, m+n=13 to 32, and p=0 to 2; and X is a halogen atom selected from I, Br and Cl, or is an alkoxy group.

2. The terminal perfluoroalkylsilane compound of claim 1 wherein X is methoxy or ethoxy.

3. A ω-trifluoroalkylsilane compound having the general formula;

$$CF_3(CH_2)_nSi(CH_3)_pX_{3-p}$$

wherein n and p are each integers; n=12 to 31 and p=0 to 2; and X is a halogen atom selected from I, Br and Cl, or is an alkoxy group.

4. The ω-trifluoroalkylsilane compound of claim 3 wherein X is methoxy or ethoxy.

* * * * *